United States Patent
Tesic et al.

(10) Patent No.: US 10,251,622 B2
(45) Date of Patent: Apr. 9, 2019

(54) SYSTEM FOR PROVIDING SCANNING MEDIUM

(71) Applicant: Delphinus Medical Technologies, Inc., Novi, MI (US)

(72) Inventors: Mike Tesic, Novi, MI (US); Marc Orloff, Novi, MI (US); Kevin Obrigkeit, Novi, MI (US); David Kunz, Novi, MI (US); Roman Janer, Novi, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 0 days.

(21) Appl. No.: 16/113,863

(22) Filed: Aug. 27, 2018

(65) Prior Publication Data

US 2019/0008478 A1    Jan. 10, 2019

Related U.S. Application Data

(62) Division of application No. 14/811,316, filed on Jul. 28, 2015, now Pat. No. 10,076,304.

(60) Provisional application No. 62/029,696, filed on Jul. 28, 2014.

(51) Int. Cl.
*A61B 8/00* (2006.01)
*A61B 5/01* (2006.01)
*A61B 8/08* (2006.01)
*A61B 8/13* (2006.01)
*A61B 5/00* (2006.01)

(52) U.S. Cl.
CPC ............ *A61B 8/406* (2013.01); *A61B 5/0091* (2013.01); *A61B 8/0825* (2013.01); *A61B 8/4281* (2013.01); *A61B 8/4461* (2013.01); *A61B 8/4494* (2013.01); *A61B 5/01* (2013.01); *A61B 8/13* (2013.01)

(58) Field of Classification Search
CPC ....... A61B 5/0091; A61B 5/01; A61B 8/0825; A61B 8/13; A61B 8/406; A61B 8/4281; A61B 8/4461; A61B 8/4494
See application file for complete search history.

(56) References Cited

U.S. PATENT DOCUMENTS

| | | |
|---|---|---|
| 4,206,763 A | 6/1980 | Pedersen |
| 6,102,857 A | 8/2000 | Kruger |
| 7,494,466 B2 | 2/2009 | Chauhan et al. |

(Continued)

*Primary Examiner* — Michael T Rozanski
(74) *Attorney, Agent, or Firm* — Wilson Sonsini Goodrich & Rosati

(57) ABSTRACT

A system for providing scanning medium for scanning a volume of tissue comprising: an inner chamber that contains the scanning medium; a transducer mounted to the inner chamber and configured to move along a motion path, with the inner chamber, in scanning the volume of tissue; an outer chamber concentrically aligned about the inner chamber to guide the inner chamber along the motion path; a piston module defining a base surface within the inner chamber, the piston module comprising a medium inlet and a medium outlet for adjusting an amount of the scanning medium within the inner chamber; a detection subsystem coupled to the base surface of the piston module; and an actuator comprising a stationary portion mounted to the piston module and a moving portion coupled to the inner chamber and configured to produce motion of the inner chamber along the motion path.

19 Claims, 11 Drawing Sheets

(56) References Cited

U.S. PATENT DOCUMENTS

| | | |
|---|---|---|
| 7,699,783 B2 | 4/2010 | Hanover et al. |
| 7,771,360 B2 * | 8/2010 | Johnson .............. A61B 5/4312 |
| | | 600/459 |
| 9,113,835 B2 | 8/2015 | Li |
| 10,076,304 B2 | 9/2018 | Tesic et al. |
| 2004/0064046 A1 * | 4/2004 | Shehada .............. A61B 8/0825 |
| | | 600/437 |
| 2006/0009693 A1 | 1/2006 | Hanover et al. |
| 2011/0105900 A1 | 5/2011 | Entrekin |
| 2013/0204136 A1 | 8/2013 | Duric et al. |
| 2013/0303895 A1 | 11/2013 | Littrup et al. |
| 2014/0235962 A1 | 8/2014 | Yu et al. |
| 2014/0276068 A1 | 9/2014 | Szpak et al. |

* cited by examiner

MOVING INNER CHAMBER-MOVING SEAL

MOVING INNER CHAMBER-STATIONARY SEAL

Strainer Washer

SYSTEM FOR PROVIDING SCANNING MEDIUM

CROSS-REFERENCE TO RELATED APPLICATIONS

This application is a divisional application of U.S. patent application Ser. No. 14/811,316, filed Jul. 28, 2015, now U.S. Pat. No. 10,076,304, which claims the benefit of U.S. Provisional Application No. 62/029,696, filed Jul. 28, 2014, which are incorporated in their entirety herein by reference.

TECHNICAL FIELD

This invention relates generally to the medical technology field, and more specifically to a new and useful system for controlling scanning medium in the medical technology field.

BACKGROUND

Early detection of breast cancer and other types of cancer typically result in a higher survival rate. Despite a widely accepted standard of mammography screenings for breast cancer detection, there are many reasons that cancer is often not detected early. One reason is low participation in breast screening, as a result of factors such as fear of radiation and discomfort. In particular, the mammography procedure involves compression of the breast tissue between parallel plates to increase the X-ray image quality by providing a more uniform tissue thickness and stabilizing the tissue. However, this compression is typically uncomfortable, or even painful. Mammography has additional drawbacks, such as limited performance among women with dense breast tissue and a high rate of "false alarms" that lead to unnecessary biopsies that are collectively expensive and result in emotional duress in patients.

Ultrasound tomography is one imaging modality in development that may be a practical alternative to mammography. However, there is a need in ultrasound tomography applications to provide a system that controls provision of a scanning medium in a robust manner. This invention provides such a new and useful system for providing scanning medium.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. System

Figure 1A:
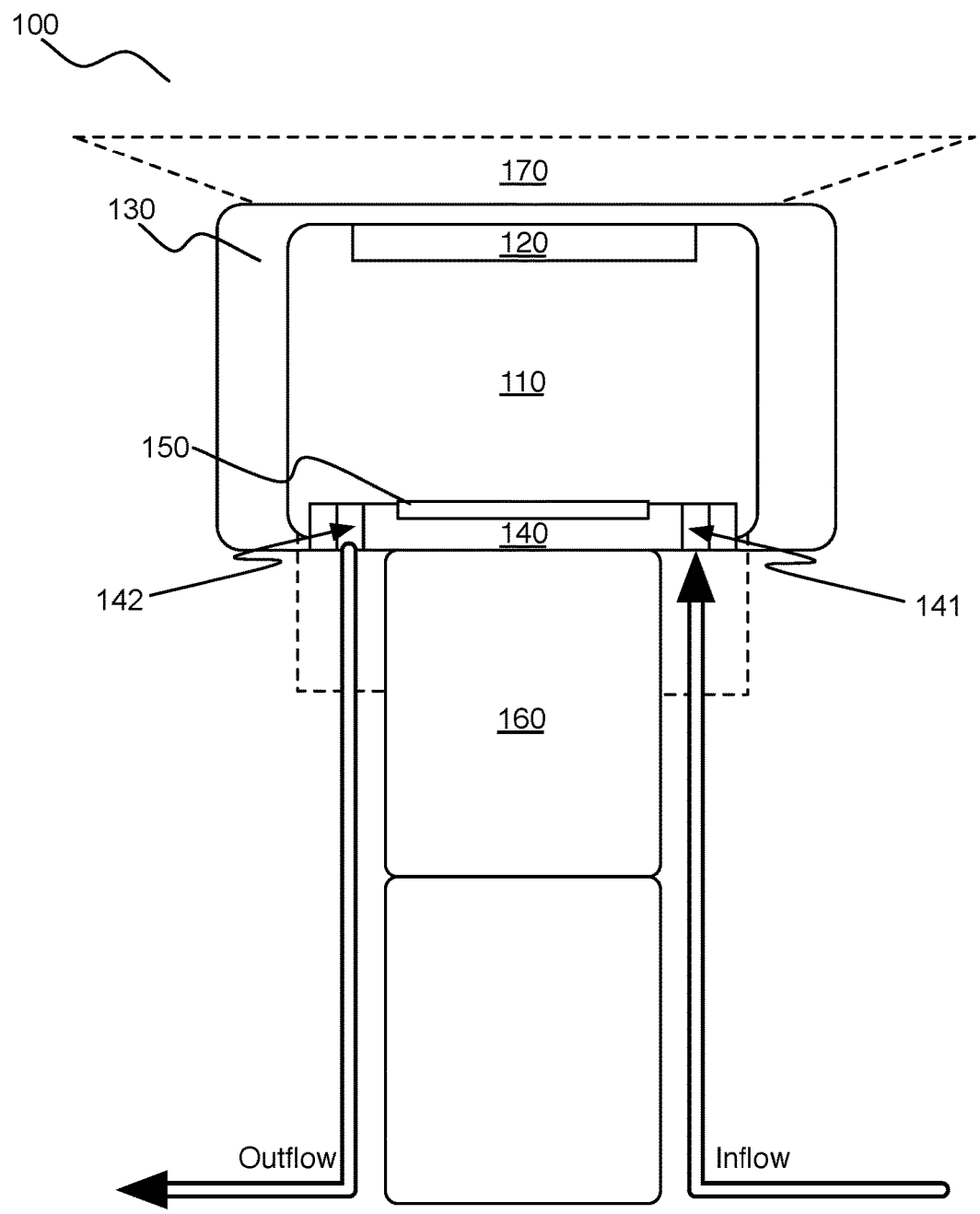
FIGS. 1A and 1B depict schematics of embodiments of a system for providing scanning medium.
Figure 1B:
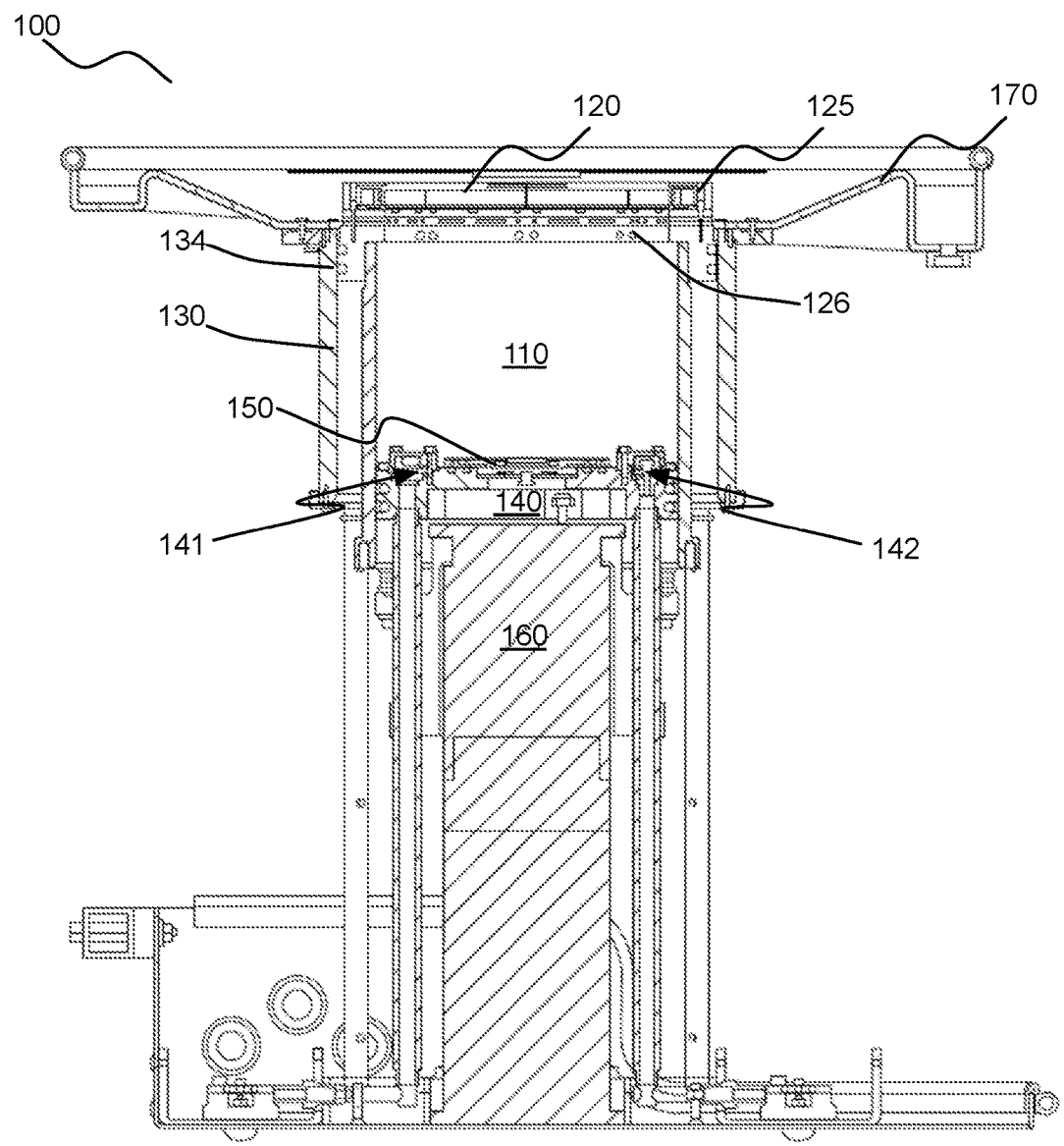

As shown in FIGS. 1A and 1B, an embodiment of a system 100 for providing a scanning medium in facilitating scanning of a volume of tissue of a patient includes: an inner chamber 110 defining a medium volume for containment of the scanning medium 112; a transducer 120 mounted to the inner chamber 110 and configured to move along a motion path, with the inner chamber, in scanning the volume of tissue; an outer chamber 130 concentrically aligned about the inner chamber 110 to guide the inner chamber along the motion path; a piston module 140 defining a base surface 142 within the inner chamber 110, the piston module 140 comprising a medium inlet 141 and a medium outlet 142 for adjusting an amount of the scanning medium within the inner chamber; a detection subsystem 150 coupled to the base surface of the piston module 140; and an actuator 160 comprising a stationary portion mounted to the piston module, and a moving portion coupled to the inner chamber and configured to produce motion of the inner chamber along the motion path. The system 100 can further comprise a patient support surface 170 coupled to the outer chamber 130 and having an opening that facilitates reception of the volume of tissue into the inner chamber 110.

Figure 2A:
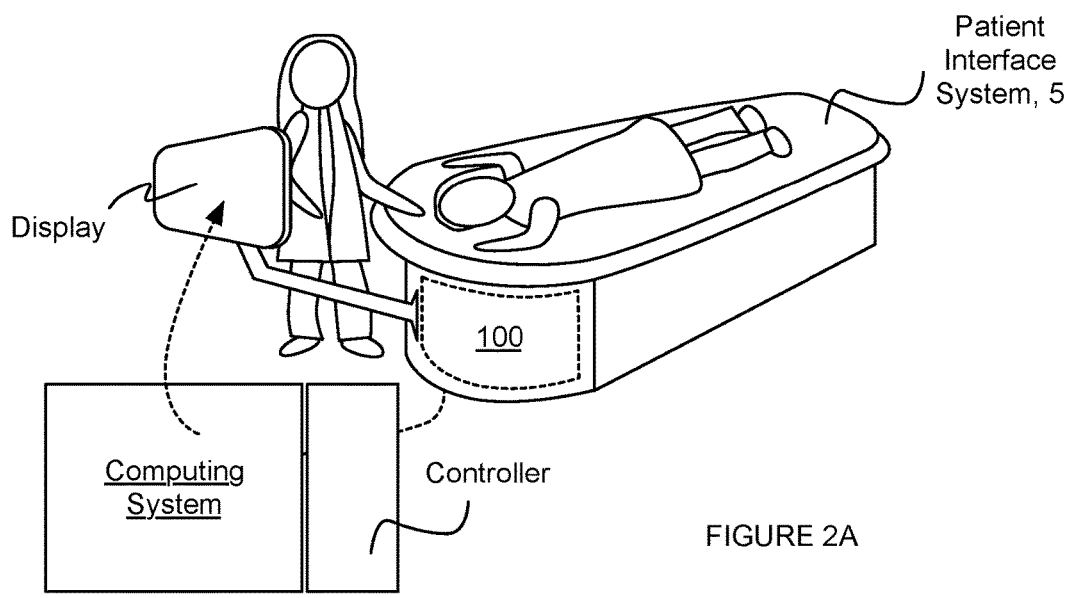
FIGS. 2A and 2B depict schematics of embodiments of a patient interface system that interfaces with a system for providing scanning medium.
Figure 2B:
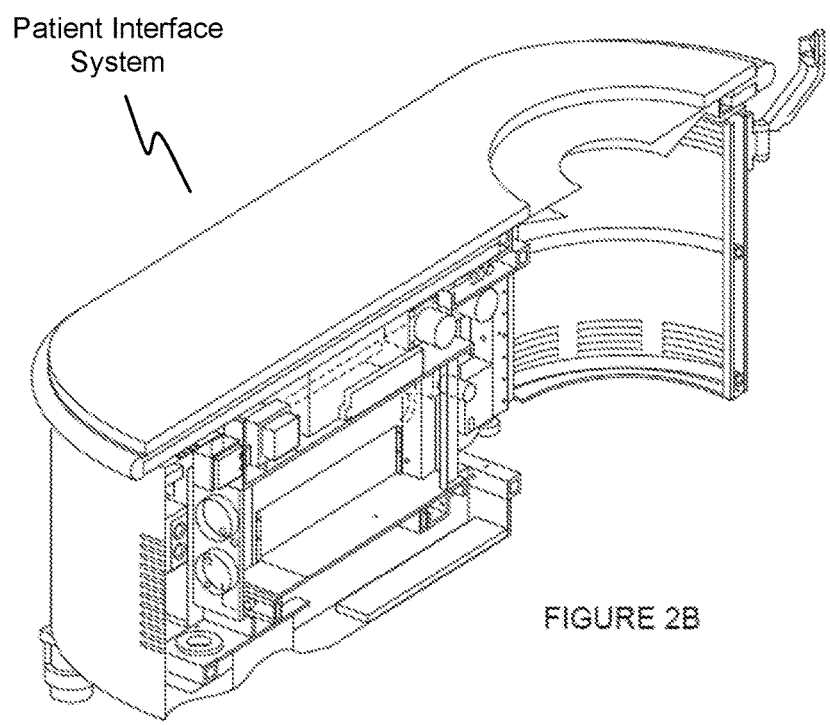
Figure 2C:
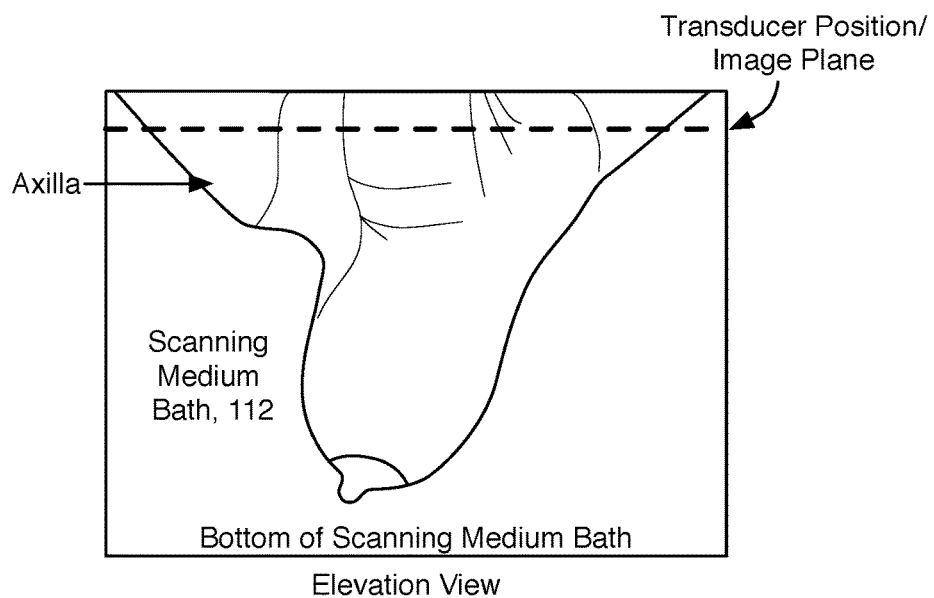
FIGS. 2C and 2D depict elevation views of a volume of tissue of a patient within a portion of an embodiment of the system for providing scanning medium.
Figure 2D:
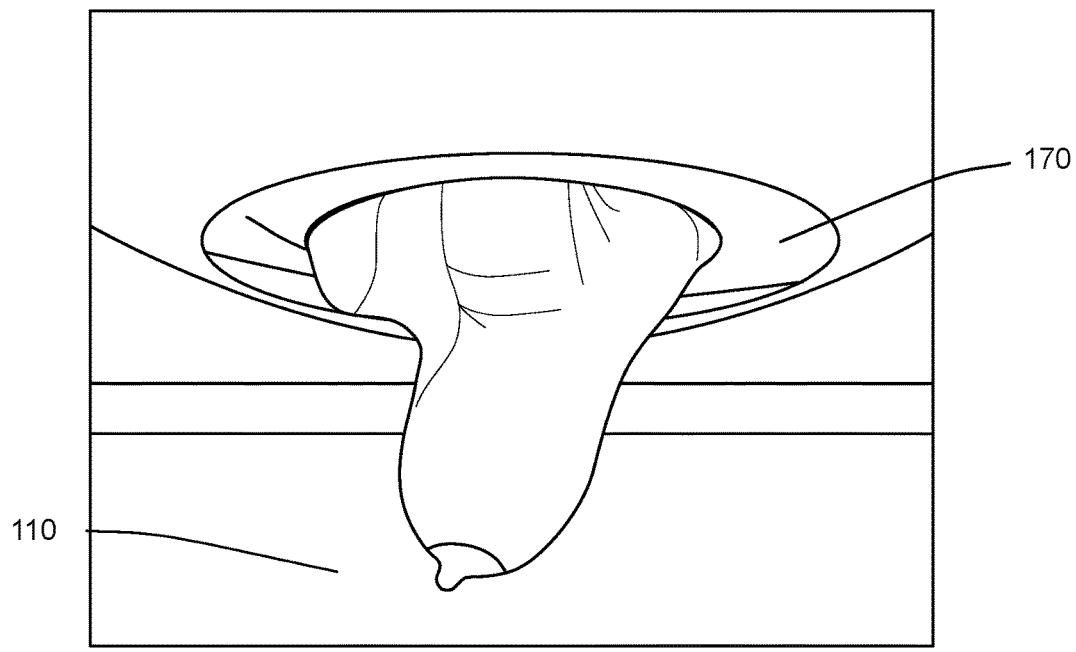

The system 100 functions to control a tissue scanning device (e.g., an ultrasound transducer), in communication with a volume of a scanning medium, in order to facilitate scanning of a volume of tissue submerged in the scanning medium. In particular, the system 100 is configured to enable motion of a chamber containing a scanning medium relative to a volume of tissue of a patient, while preventing leakage of the scanning medium and other system malfunctions. The system 100 can also function to facilitate a reduction in the amount of unnecessary scans taken (e.g., due to patient misalignment). In one embodiment, as shown in FIGS. 2A and 2B, the system 100 can be provided along with a patient interface system 5 configured interface with (e.g., be placed over, surround) the system 100 for providing a scanning medium, which receives the volume of tissue extending through an aperture of the patient interface system. The system 100, as shown in FIG. 2A, can further be in communication with a controller and a computing system configured to process information from the system 100 and render information derived from the system 100 at a display. As shown in FIGS. 2C and 2D, embodiments of the system 100 preferably allow access to a patient's chest wall and axilla, in order to facilitate scanning of a protruding tissue of the patient (e.g., breast tissue). However, the system 100 can additionally or alternatively coordinate with any other suitable element(s) that facilitate scanning of a volume of tissue of a patient. Furthermore, the system 100 is preferably configured to facilitate ultrasound scanning of a volume of tissue of a patient, but variations of the system 10o can additionally or alternatively be configured to facilitate any other suitable modality of tissue scanning making use of a scanning medium in which the volume of tissue is at least partially submerged. In variations, the system 100 can include or otherwise interface with elements of the patient interface system described in U.S. application Ser. No. 14/208,181 entitled "Patient Interface System" and filed on 13 Mar. 2014, some variations of which are described in further detail below; however, the system 100 can additionally or alternatively interface with any other suitable element(s) that facilitate scanning of a volume of tissue of the patient.

1.1 System—Inner Chamber and Transducer

The inner chamber 110 defines a medium volume for containment of the scanning medium 112 (shown in FIG. 2C), and is preferably mounted to a transducer 120 that scans the volume of tissue along a motion path. The inner chamber 110 functions to provide a volume of scanning medium that surrounds one or more regions of the volume of tissue undergoing scanning, and further to allow actuation of the transducer 120 in relation to the volume of tissue being scanned. The scanning medium is preferably water, such that the inner chamber 110 provides a water bath for acoustic coupling with the volume of tissue in operation; however, the scanning medium can additionally or alternatively comprise any other suitable acoustic coupling medium that facilitates ultrasound scanning. For instance, the scanning medium can comprise a hydrogel material or any other suitable scanning medium. In variations of the system 100 adapted for imaging modalities aside from ultrasound, the scanning medium can comprise any other suitable scanning medium, or alternatively, the system 100 can omit use of a scanning medium (e.g., other than air).

The inner chamber 110 preferably defines a substantially cylindrical volume to contain the scanning medium and to receive the volume of tissue of the patient; however, the inner chamber 110 can alternatively define any other suitable volume morphology for scanning medium containment and/or tissue volume reception. The medium volume defined by the inner chamber 110 is preferably substantially larger (e.g., 5-10× larger) than the volume of tissue intended to be scanned; however, the medium volume can alternatively have any other suitable volumetric capacity. The inner chamber 110 is further preferably composed of a material that is one or more of: able to be sanitized or cleaned (e.g., after each patient interaction, etc.), resistant to damage by the scanning medium being used (e.g., corrosion proof, corrosion resistant), low friction (e.g., to facilitate motion of the inner chamber 110 during actuation), and characterized with sufficient mechanical properties (e.g., stiffness, compliance, thermal expansion coefficient, etc.) to support the weight of the scanning medium within the inner chamber 110. However, the inner chamber 110 can additionally or alternatively have any other suitable properties. In a specific example, the inner chamber 110 is a cylindrical chamber composed having a low friction and corrosion-proof inner surface that supports the scanning medium during actuation of the inner chamber 110 relative to other elements of the system 100, and that has a suitable coefficient of thermal expansion to maintain necessary waterproof seals at interfaces between the inner chamber 110 and other elements of the system 100.

The inner chamber 110 is preferably configured to move along a linear path, as enabled by the actuator 160 described below, in transmitting the transducer 120 along a linear motion path. As such, motion of the inner chamber 110, with the transducer 120, in a posterior-anterior direction relative to a volume of tissue of the user, can enable scanning of an entire volume of tissue of a patient in a consistent manner. However, the inner chamber 110 can alternatively be configured to move along any other suitable path(s) in relation to other elements of the system 100, in facilitating scanning of the patient's tissue. For instance, the inner chamber 110 can be guided along a non-linear path that corresponds to a shape of a volume of tissue being scanned.

The transducer 120 is preferably an ultrasound ring transducer comprising elements configured to emit acoustic signals toward a volume of tissue within the inner chamber 110 and/or elements configured to receive acoustic signals (e.g., scattered acoustic signals, reflected acoustic signals, transmitted acoustic signals, etc.) from the volume of tissue, in order to generate a rendering of the volume of tissue. The elements of the ring transducer 120 can be configured to form an enclosed perimeter about the volume of tissue (e.g., within a scanning plane), and in one specific example, can form a circular perimeter about the volume of tissue. However, the elements of the transducer 120 can alternatively be configured in any other suitable manner. For instance, the elements can form one or more of: a closed boundary (e.g., polygonal boundary, ellipsoidal boundary, etc.), an open boundary (e.g., semi-circular boundary, open curvilinear boundary, open linear boundary, etc.), and a surface about the volume of tissue.

In variations of the transducer 120 comprising an ultrasound ring transducer, the transducer elements can comprise any one or more of: piezoelectric elements, capacitive elements (e.g., capacitive micromachined ultrasonic transducer elements), and any other type of ultrasound element. However, the transducer 120 can be configured with any other suitable elements that enable generation of a rendering of the volume of tissue. The transducer 120 can be an embodiment of a transducer 120 as described in one or more of: U.S. application Ser. No. 13/368,169 entitled "System and Method for Imaging a Volume of Tissue" and filed on 7 Feb. 2012, U.S. application Ser. No. 13/756,851 entitled "System and Method for Imaging a Volume of Tissue" and filed on 1 Feb. 2013, and U.S. application Ser. No. 13/894,202 entitled "System and Method for Performing an Image-Guided Biopsy" and filed on 14 May 2013, which are each incorporated herein in its entirety by this reference, or any other suitable transducer 120. Furthermore, embodiments of the system 100 can additionally or alternatively enable access to and scanning of any other suitable tissue (e.g., non-breast tissue) of a patient.

Figure 3A:
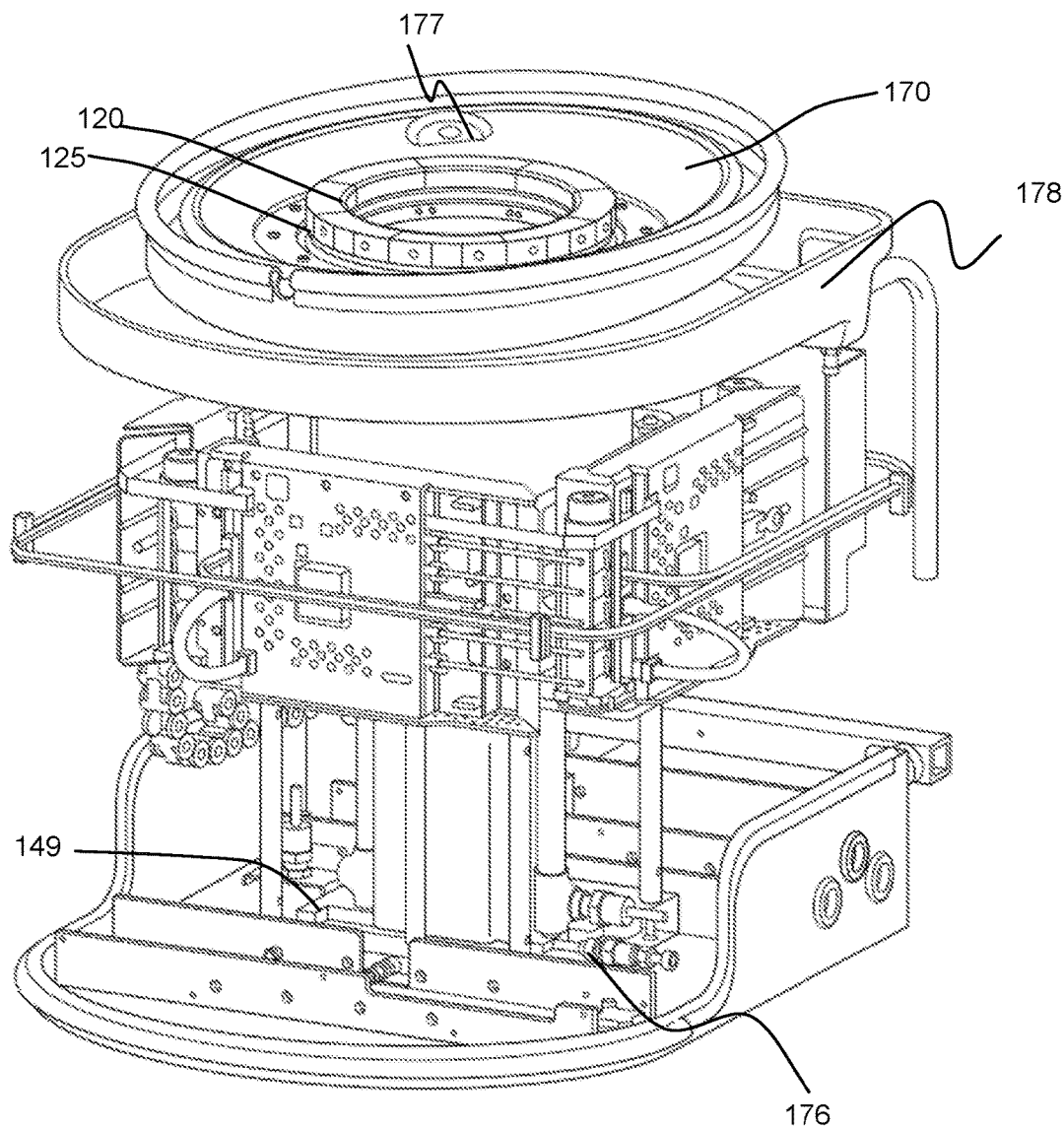
FIGS. 3A and 3B depict specific examples of a portion of an embodiment of a system for providing scanning medium.

The transducer 120, in cooperation with motion of the inner chamber 110 preferably provides complete access to the volume of tissue being scanned. For instance, the transducer 120 can be configured to provide access to a volume of breast tissue from the nipple region entirely to the chest wall of the patient. In one variation, the ring transducer 120 can be coupled to a superior portion of the inner chamber 110 (e.g., in the orientation shown in FIGS. 1A and 1B), by way of a transducer mount 125, as shown in FIG. 3A. In this variation, the transducer mount 125 or the inner chamber 110 can circumscribe the other one of the inner chamber 110 and the transducer mount 125, wherein the transducer mount 125 couples to the transducer 120 while enabling the volume of tissue to access the inner chamber 110, through the transducer 120. Furthermore, the transducer mount 125 can include a set of openings 126 that allow scanning medium drainage and/or prevent scanning medium trapping (e.g., between elements of the system) as the inner chamber 110 travels along the motion path. In a specific example, the transducer mount 125 includes a set of openings 126 circumferentially arranged between a superior portion of the inner chamber 110 and the transducer 120, such that scanning medium weeping can occur from a region inferior to the transducer 120 (in the orientation shown in FIG. 1B). The set of openings 126 can, however, be arranged relative to the transducer 120, the transducer mount 125, and the inner chamber 110 in any other suitable manner.

Figure 3B:
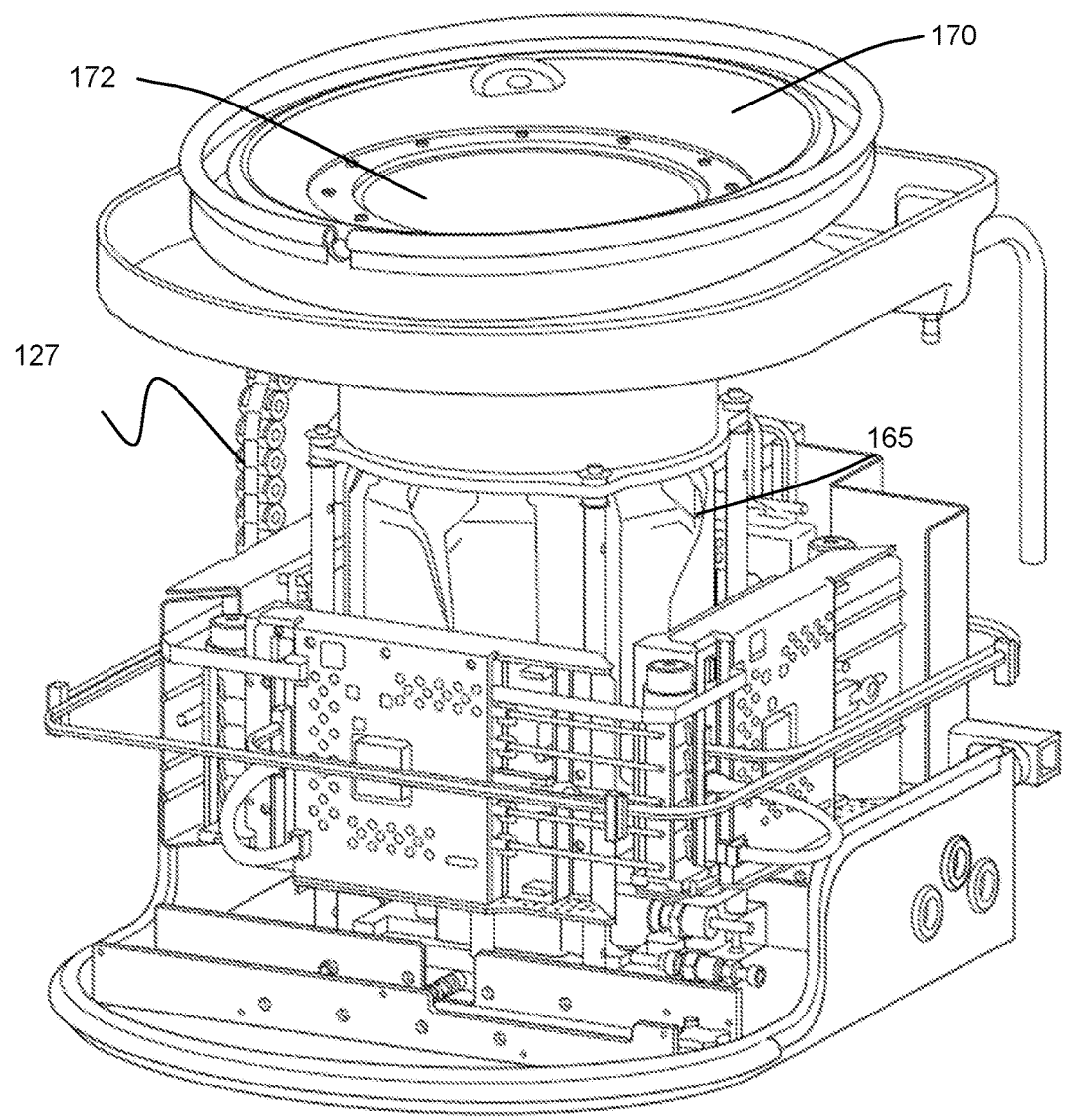

Additionally, in variations wherein the transducer 120 is configured to move along a motion path (e.g., as enabled with the inner chamber), the ring transducer 120 can be electrically coupled to a control module for the system by way of an electromechanical coupler 127 (e.g., cable carrier), as shown in FIG. 3B, configured to enable motion of the ring transducer while providing consistent electrical communication between the transducer 120 and the control module. However, the inner chamber 110, the transducer 120, and/or the transducer mount 125 can alternatively be configured in any other suitable manner. Furthermore, in relation to the volume of scanning medium within the inner chamber 110, the volume of scanning medium can be adjusted as the transducer 120 moves along the motion path by way of a medium inlet 141 and/or a medium outlet 142 (as described in further detail below). For instance, in one variation, the system 100 can be configured to increase a level of the scanning medium within the inner chamber 110 as the transducer 120 moves in a superior direction, and the system 100 can be configured to decrease the level of the scanning medium within the inner chamber 110 as the transducer 120 moves in an inferior direction. As such, this variation, motion of the transducer 120 can be coordinated with the level of scanning medium within the inner chamber, in providing scanning medium that surrounds the volume of tissue in operation. Additionally or alternatively, the system 100 can be configured to maintain a substantially constant volume of the scanning medium within the inner chamber 110.

1.2 System—Outer Chamber

The outer chamber 130 is configured to surround at least a portion of the inner chamber 120, and functions to guide the inner chamber along the motion path, in facilitating scanning of the volume of tissue. Preferably, the outer chamber 130 is concentrically aligned about the inner chamber 110; however, the outer chamber 130 and the inner chamber 110 can have any other suitable alternative relationship in relation to surrounding of the inner chamber 110. Similar to the inner chamber 110, the outer chamber 130 preferably defines a substantially cylindrical volume that surrounds the inner chamber 110; however, the outer chamber 130 can alternatively define any other suitable volume morphology that allows the inner chamber 110 to be guided along the motion path. The outer chamber 130 is preferably a substantially stationary element of the system, and as such, is preferably not coupled to the actuator 160 described below; however, the outer chamber 130 can alternatively be configured to move along any suitable path(s) in relation to other elements of the system 100, in facilitating scanning of the patient's tissue.

Figure 4A:
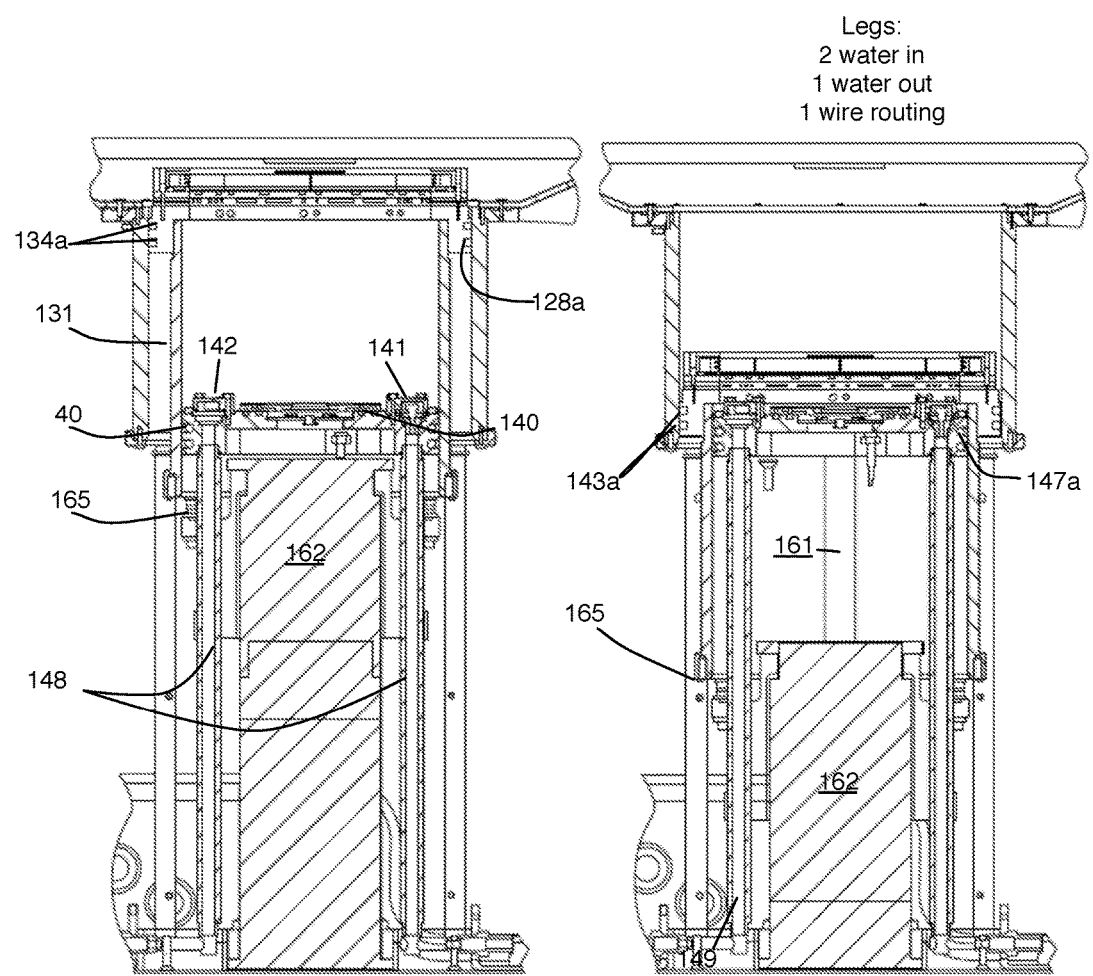
FIG. 4A depicts a specific example of two configurations of a system for providing scanning medium.

The outer chamber 130 preferably defines a region 131, as shown in FIG. 4A, that is at least partially isolated from the scanning medium. In variations, the region 131 can be defined between the inner chamber 110 and the outer chamber 130, and in one variation, the interior wall (e.g., cylindrical wall) of the outer chamber 130 can be displaced from the exterior wall (e.g., cylindrical wall) of the inner chamber 110 (e.g., by a constant offset) to define the region 131. As such, in the example shown in FIG. 4A, an annular prismatic (e.g., circular annular prismatic) region 131 between the outer chamber 130 and the inner chamber 110 can be isolated from scanning medium within the inner chamber 110, thus providing a "dry" space for electrical coupling elements (e.g., an electromechanical coupler 127 and/or any other elements of the system suited for a dry environment. In one variation, as shown in FIG. 4A, electrical circuitry and electrical coupling elements of the transducer ring 120 can be configured to pass into an annular prismatic "dry" region defined by the outer chamber 130, thus isolating them from the scanning medium. To further promote dryness in the region 131 defined between the outer chamber 130 and the inner chamber 110, the outer chamber 130 can be coupled to or otherwise in communication with any suitable heating elements to heat the region 131 and evaporate any moisture within the region 131. Additionally or alternatively, the region 131 can include a desiccant material (e.g., silica gel) that absorbs moisture in the event that moisture from the scanning medium enters the region 131.

In variations wherein the outer chamber 130 defines a region 131 isolated from the scanning medium, at least one of the inner chamber 110, the transducer piston 125 coupled to the transducer ring 120, and the outer chamber 130 can include a seal 134, as shown in FIG. 1B, configured circumferentially about a surface of one or more of: the inner chamber 110, the transducer mount 125, and the outer chamber 130 to provide a hermetic seal that prevents fluid leakage into the region 131.

In one variation, as shown in FIG. 4A, the transducer mount 125 can include a circumferential groove 128a at an outer surface configured to receive an X-ring seal 134a that does not roll during motion of the inner chamber 110, while providing a hermetic seal between the outer chamber 130 and the transducer mount 125. As such, the seal 134a in this configuration is indirectly coupled to the inner chamber 110 and in contact with the outer chamber 130, to isolate the region 131 defined between the outer chamber 130 and the inner chamber 110 from the scanning medium as the inner chamber moves along the motion path. However, in alternatives of this variation, the seal 134 can be directly coupled between the inner chamber 110 and the outer chamber 130 in isolating the region 131 from scanning medium.

Figure 4B:
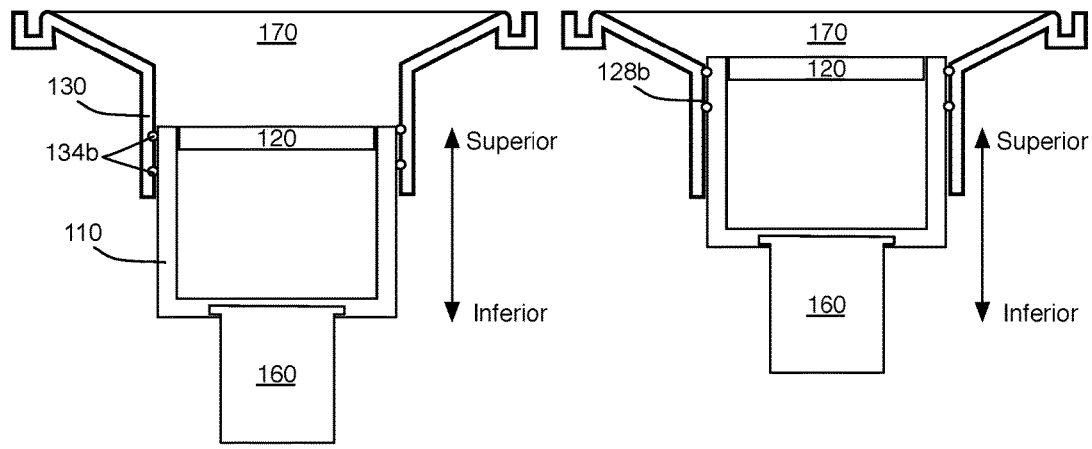
FIGS. 4B-4D depict variations of a portion of a system for providing scanning medium.
Figure 4C:
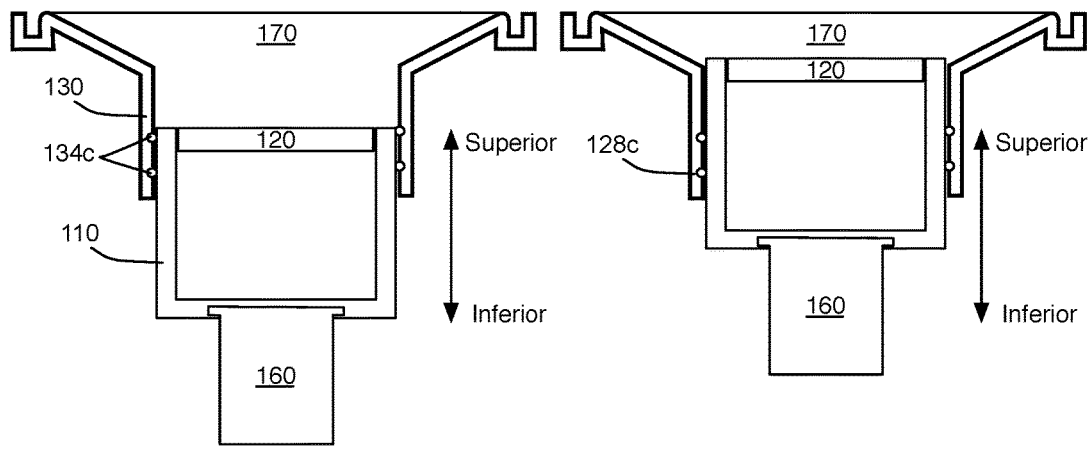
Figure 4D:
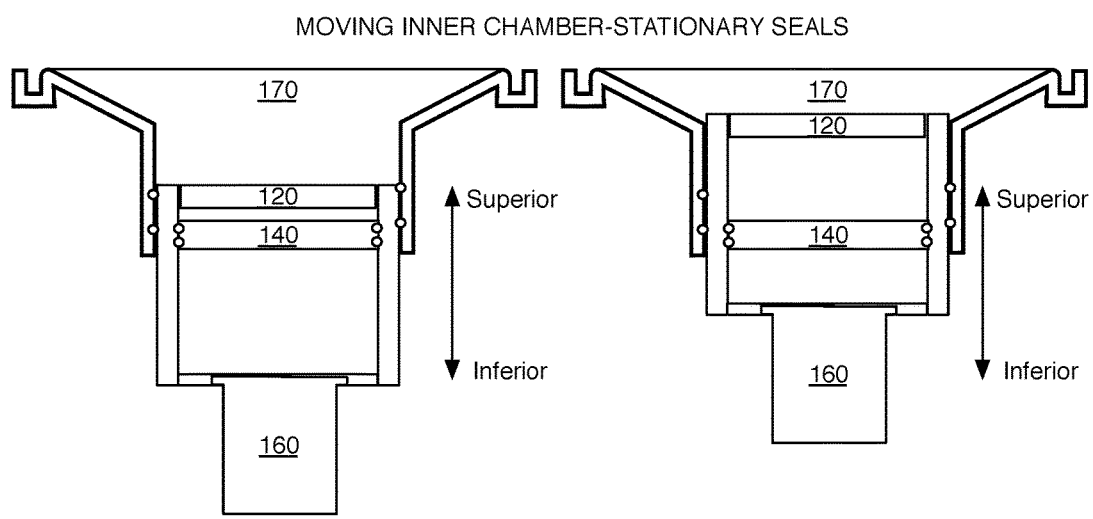

In another variation, as shown in FIG. 4B, the inner chamber 110 can include a circumferential groove 128b at an outer surface configured to receive an O-ring or X-ring seal 134b that provides a hermetic seal during motion of the inner chamber 110 along the motion path. Additionally or alternatively, in yet another variation, as shown in FIG. 4C, the outer chamber 130 can include a circumferential groove 128c about an inner surface configured to receive an O-ring or X-ring seal 134c that provides a hermetic seal during motion of the inner chamber 110 (while the outer chamber 130 and its O-ring/X-ring are substantially stationary). The system 100 can, however, include any other suitable variation of the seal 134 in isolating the region 131 defined between the outer chamber 130 and the inner chamber 110 from the scanning medium. As such, the seal 134 can be configured to move with the inner chamber 110 along the motion path, or can be configured to be stationary during motion of the inner chamber 110 (e.g., relative to the piston module 140 and the outer chamber 130), one example of which is shown in FIG. 4D.

Additionally or alternatively, the system 100 can include any other suitable sealing elements (e.g., sealing compounds, rolling diaphragms, etc.) configured to provide a hermetic seal to define a volume isolated from scanning medium within the inner chamber 110. Furthermore, surfaces of the outer chamber 130, transducer mount 125, inner chamber 110, and/or any other element of the system 100 involved in forming the isolated "dry" region 131 are preferably processed to reduce surface roughness, thereby reducing sliding friction produced between elements. In a specific example, such surfaces can be nickel-plated with Teflon impregnation; however, variations of the specific example can include any other suitable surface treatments or use of materials (e.g., stainless steel, plastic) that reduces sliding friction. Furthermore, the outer chamber 110, transducer mount 125, and/or the inner chamber 110 can alternatively be configured in any other suitable manner.

1.3 System—Piston Module and Detection Subsystem

As shown in FIGS. 1A and 1B, the piston module 140 defines a base surface within the inner chamber 110, and can comprise a medium inlet 141 and a medium outlet 142 that enable inflow and outflow of the scanning medium into and from the inner chamber 110. In some variations, the piston module 140 can additionally or alternatively be coupled to a detection subsystem 150.

The piston module 140 functions to facilitate regulation of an amount of scanning medium within the inner chamber 110, and can additionally or alternatively function to facilitate sensing/indication of environmental parameters related to the system 110. The piston module 140 is preferably a stationary element of the system 100, such that the inner chamber 110 moves about a stationary piston module 140; however, the piston module 140 can alternatively be configured to move along any suitable path. For instance, the piston module 140 can move, with the inner chamber 110, in modulating a level of the scanning medium within the inner chamber 110. Furthermore, the piston module 140 preferably defines an inferior base surface within the inner chamber 110, but can additionally or alternatively define any other suitable surface in relation to the inner chamber 110.

An interface 40 between the piston module 140 and the inner chamber 110 is preferably hermetically sealed to facilitate containment of the scanning medium within the inner chamber 110. In particular, the interface between the piston module and the inner chamber is preferably hermetically sealed as the inner chamber moves along the motion path, such that the scanning medium does not leak from the inner chamber as the inner chamber 110 moves along the motion path. As such, the piston module 140 and/or the inner chamber 110 can include elements that facilitate generation of a hermetic seal at a junction between the inner chamber 110 and the piston module 140. In a first variation, the piston module 140 comprises a circumferential groove 147a at an exterior portion of the piston module 140 configured to receive an X-ring or an O-ring seal 143a that provides a hermetic seal to contain the scanning medium during motion of the inner chamber 110. However, the piston module 140 and/or the inner chamber 110 can be configured to provide a hermetic seal with any other alternative or additional elements (e.g., sealing compounds, rolling diaphragms, etc.). Surfaces of the piston module 140 and/or the inner chamber 110 are preferably processed to reduce surface roughness, thereby reducing sliding friction produced between elements. In a specific example, similar to that described above in relation to relative motion of the inner chamber 100 and the outer chamber 130, such surfaces can be nickel-plated with Teflon impregnation; however, variations of the specific example can include any other suitable surface treatments or use of materials (e.g., stainless steel, plastic) that reduces sliding friction. Furthermore, the piston module 140 and/or the inner chamber 110 can alternatively be configured in any other suitable manner.

Figure 5:
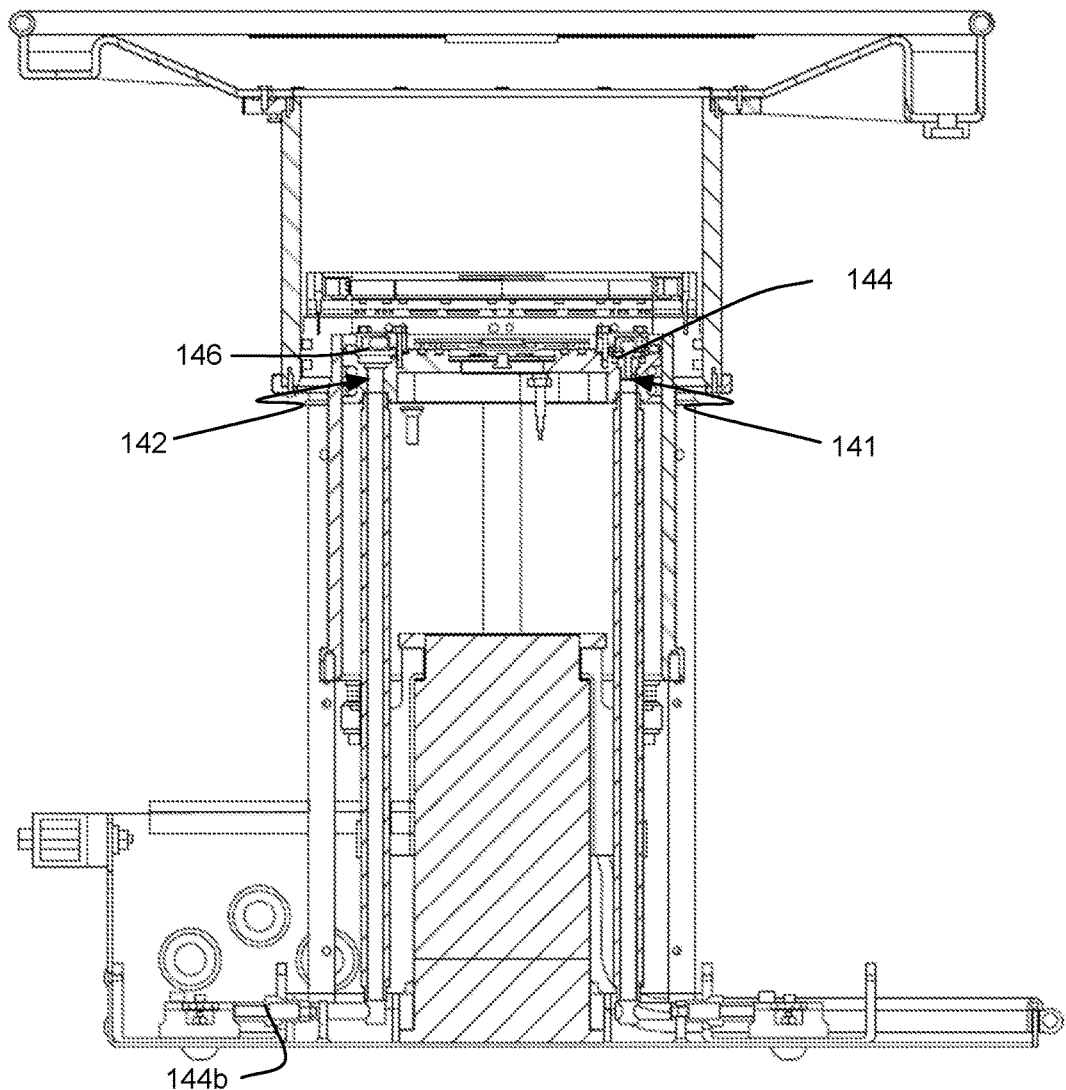
FIG. 5 depicts specific examples of elements of an embodiment of a system for providing scanning medium.

The medium inlet 141 is preferably an opening into the inner chamber 110 through the piston module 140, and functions to enable inflow of the scanning medium into the inner chamber 110. As such, in the orientation shown in FIGS. 4A and 5, the medium inlet 141 allows the inner chamber 110 to be filled from an inferior (e.g., bottom) portion of the inner chamber 110. However, medium inlet 141 can additionally or alternatively be configured to deliver scanning medium into any other suitable portion of the inner chamber (e.g., through a vertical wall of the inner chamber, etc.). In variations wherein the medium inlet 141 is an opening of the piston module 140, the medium inlet 141 can be defined through the thickness of the piston module 140, or can alternatively define an opening into the inner chamber 110 in any other suitable manner. Preferably, the medium inlet 141 is positioned at a peripheral region of the piston module 140, as shown in FIGS. 4A and 5. However, the medium inlet 141 can alternatively be positioned at any other suitable non-peripheral region of the piston module 140.

Figure 6:
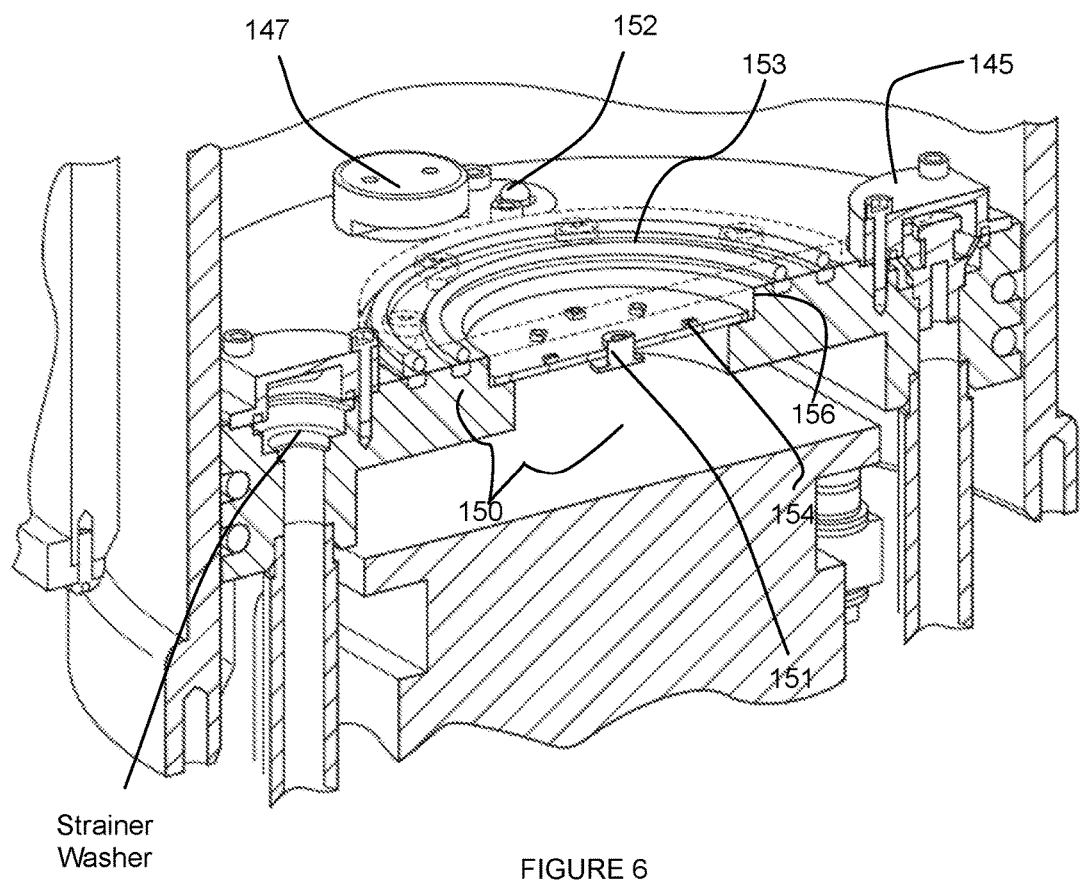
FIG. 6 depicts specific examples of a piston module and detection subsystem of an embodiment of a system for providing scanning medium.

As shown in FIG. 5, the medium inlet 141 is preferably a valved opening, and preferably comprises a check valve 144 configured to prevent backflow (e.g., of contaminated scanning medium) of contents of the inner chamber 110 from the inner chamber 110 in a reverse direction. However, the medium inlet 141 can alternatively omit a valve or can prevent backflow in any other suitable manner. In some variations, as shown in FIG. 6, the medium inlet 141 can be configured to transmit the scanning medium through a fitting 145 that directs the scanning medium laterally into the inner chamber 110, thereby preventing a vertical stream of scanning fluid into the inner chamber that can disturb the scanning process, wherein the fitting 145 also functions to trap air bubbles that may be generated during scanning of the volume of tissue of the patient. However, the medium inlet 141 can be configured to transmit the scanning medium through any other fitting that directs fluid flow in any other suitable manner, or can be configured to transmit the scanning medium without a fitting.

Similar to the medium inlet 141, the medium outlet 142 is preferably an opening from the inner chamber 110 through the piston module 140, and functions to enable outflow of the scanning medium from the inner chamber 110. As such, in the orientation shown in FIGS. 4A and 5, the medium outlet 142 allows the inner chamber 110 to be drained from an inferior (e.g., bottom) portion of the inner chamber 110. However, medium outlet 142 can additionally or alternatively be configured to allow outflow of scanning medium from any other suitable portion of the inner chamber (e.g., through a vertical wall of the inner chamber, etc.). In variations wherein the medium outlet 142 is an opening through the piston module 140, the medium outlet 142 can be defined through the thickness of the piston module 140, or can alternatively define an opening from the inner chamber 110 in any other suitable manner. Preferably, the medium outlet 142 is positioned at a peripheral region of the piston module 140, as shown in FIGS. 4A and 5. However, the medium outlet 142 can alternatively be positioned at any other suitable non-peripheral region of the piston module 140. Furthermore, as shown in FIG. 5, the medium outlet 142 can be in communication with a check valve 144b that prevents potentially contaminated scanning medium from backflowing into the system 100.

In some variations, a surface of the piston module 140 facing the interior of the inner chamber 110 can be configured to direct fluid flow toward the medium outlet 142, for instance, by providing a graded surface. The medium outlet 142 is preferably an opening with filtering capacity, and preferably comprises a strainer washer 146 configured to prevent undesired material within the inner chamber 110 from passing through the medium outlet 142, as shown in FIG. 6. As such, the strainer washer 146 prevents clogging of elements downstream of the medium outlet 142. However, the medium outlet 142 can alternatively omit a straining or filtering element. In some variations, the medium outlet 142 can be configured to cooperate with a fitting that prevents undesired fluid flow from the inner chamber, which can interfere with scanning of the volume of tissue. In one such variation, as shown in FIG. 6, the fitting can comprise an anti-vortex drain fitting 147 having a slotted opening that prevents fluid eddies from forming and prevents the fitting from drawing in air. As such, the anti-vortex drain fitting 147 can accelerate fluid drainage from the inner chamber 110 and trap air bubbles that may be generated during scanning of the volume of tissue of the patient. However, the medium outlet 142 can be configured to transmit the scanning medium from the inner chamber 110 through any other fitting that directs fluid flow in any other suitable manner, or can be configured to transmit the scanning medium without a fitting.

The piston module 140 can define multiple medium inlets and/or multiple medium outlets in regulating an amount of scanning medium within the inner chamber 110. Additionally or alternatively, one or more openings into the chamber can be configured to function as both a medium inlet 141 and a medium outlet 142 in a bi-functional manner. Furthermore, the medium inlet(s) 141 and/or the medium outlet(s) 142 can be routed through structural elements of the system (e.g., hollow support legs 148 coupled to an inferior surface of the piston module 140), for compactness of the system 100. In a specific example, as shown in FIG. 4A, the piston module 140 comprises two medium inlets 141 and a single medium outlet 142, wherein the medium inlets 141 and the medium outlet 142 are routed through three hollow support legs 148, respectively coupled the piston module 140, wherein a fourth support leg provides routing of electrical components (e.g., wiring) to support the detection subsystem 150 of the piston module 140.

Furthermore, in relation to the amount of scanning medium within the inner chamber 110, the medium inlet(s) 141 and/or the medium outlet(s) 142 can be configured to cooperate with a manifold 149 fluidly coupled to the medium inlet(s) 141 and the medium outlet(s) 142 and in communication with a fluid handling system that transmits scanning medium into the medium inlet(s) 141 and out from the medium outlet(s) 142, as shown in FIG. 3A. In a specific example, the manifold 149 can be welded to fluid conduits into the medium inlet(s) 141 and to fluid conduits into the medium outlet(s) 142 of the piston module 140, as shown in FIGS. 1B and 4A. Furthermore, in the specific example, fluid delivery into the manifold 149 can involve the use of valves (e.g., drain check valves) to prevent backflow of fluid into any portion of the system 100 in an undesired manner, as shown in FIG. 5.

As indicated above, an amount of scanning medium within the inner chamber 110 can be configured to decrease as the inner chamber 110 and coupled ring transducer 120 move in a superior-to-inferior direction (e.g., in relation to the ground), such that scanning medium is only provided up to the region of the volume of tissue currently being scanned. In one such specific example, an amount of scanning medium within the inner chamber 110 can be configured to decrease at a rate of 1 gallon per inch of travel along a motion path of 6.5 inches in the superior-to-inferior-direction in relation to the ground, as the transducer 120 moves in the superior-to-inferior direction. However, the amount of scanning medium can be maintained within the inner chamber 110 during scanning of the volume of tissue. In one such variation, the scanning medium can be pumped into and drained from the inner chamber 110 as the inner chamber 110 moves in a superior-to-inferior direction and an inferior-to-superior direction, respectively. In another such variation, a surface (e.g., base surface) within the inner chamber 110 can be configured to move in opposition to motion of the inner chamber 110, thereby maintaining a level of the scanning medium within the inner chamber 110. In yet another variation, the inner chamber 110 can contain a bladder of scanning medium that is filled with scanning medium as the inner chamber 110 moves in a superior-to-inferior direction. Yet alternatively, an amount of scanning medium within the inner chamber 110 can be configured to provide any suitable level of medium in relation to the volume of tissue being scanned, as the inner chamber 110 and coupled transducer 120 move in a superior-to-inferior direction, an inferior-to-superior direction, or along any other suitable motion path.

As shown in FIGS. 1B and 6, the detection subsystem 150 is in communication with the interior of the inner chamber 110 and coupled to the piston module 140, and functions to enable environmental sensing within the inner chamber 110. Preferably, the detection subsystem 150 enables one or more of optical sensing of events within the inner chamber 110 and temperature sensing within the inner chamber 110. As such, the detection subsystem 150 can include an optical sensor 151 (e.g., of a camera) and/or a temperature sensor 152 configured to face the interior of the inner chamber 110. In one such variation, the detection subsystem 150 comprises an optical sensor 151 fluidly isolated from scanning medium within the inner chamber 110, but able to detect events within the inner chamber 110 by way of a transparent covering 153 that provides fluid isolation but light transmission. As such, the optical sensor 151 of this variation is configured to enable a volume of tissue within the inner chamber 110 to be observed (e.g., in relation to positioning of the volume of tissue within the inner chamber, etc.) during operation of the system 100. The optical sensor 151 can be configured to provide video footage and/or still images of the interior of the inner chamber 110 (e.g., during operation, etc.); however, the optical sensor 151 can alternatively be configured to provide any other suitable type of image data of the interior of the inner chamber 110.

The detection subsystem 150 can additionally or alternatively comprise indicators configured to indicate proper function of any element of the detection subsystem 150 and/or other elements of the system 100. In one such variation, as shown in FIG. 6, the detection system can include a set of light emitters 154 (e.g., LEDs) fluidly isolated from scanning medium within the inner chamber 110, but able to detect events within the inner chamber 110 by way of a transparent covering 153 that provides fluid isolation but light transmission. As such, the set of light emitters 154 can be configured proximal the optical sensor 151 for transmission of light through the transparent covering 153. In this variation, the set of light emitters 154 can function as indicators (e.g., of proper function of the system 100, of improper function of the system 100), or can additionally or alternatively function to provide illumination that facilitates optical sensing by the optical sensor 151 of the detection subsystem 150.

As noted above, the detection subsystem 150 can additionally or alternatively include a temperature sensor 152 that is in thermal communication with the interior of the inner chamber 110, thereby enabling detection of thermal conditions within the inner chamber 110 and/or temperature regulation of contents (e.g., scanning medium) of the inner chamber 110. In variations of the detection subsystem 150 comprising a temperature sensor 152, the temperature sensor is preferably configured proximal at least one of the medium inlet 141 and the medium outlet 142, thereby enabling detection of a temperature of the scanning medium as it enters/leaves the inner chamber 110. However, the temperature sensor can alternatively be configured away from the medium inlet 141 and/or the medium outlet 142, thereby enabling detection of an ambient temperature within the inner chamber 110. As such, the detection subsystem 150 can comprise multiple temperature sensors 152 configured to provide holistic information regarding temperature within regions of the inner chamber 110.

In a specific example, as shown in FIG. 6, the detection subsystem 150 comprises an optical sensor 151 centrally located within a recess 156 of a superior surface of the piston module 140, wherein the recess is covered by a transparent covering 153 (e.g., glass covering, plastic covering) that hermetically seals the optical sensor from scanning medium within the inner chamber 110 by way of a set of face-sealing O-rings. In the specific example, the detection module 150 comprises an array of light emitting diodes 154 (LEDs) surrounding the optical sensor and configured to indicate proper/improper function of the sensors of the detection subsystem 150, wherein the set of LEDs is also located proximal the optical sensor 151 within the recess. Furthermore, the detection subsystem 150 of the specific example comprises a temperature sensor 152 partially embedded at a superior surface of the piston module 140, proximal the medium outlet 142, thereby enabling detection of a temperature of the scanning medium within the inner chamber 110. Furthermore, the optical sensor 151 is configured to transmit an image dataset of the volume of tissue, during scanning, to a computing system, and the temperature sensor 152 is configured to transmit a temperature dataset associated with the scanning medium to the computing system. Thus, the computing system of the example can process the image dataset and the temperature dataset and generate an analysis, and provide information derived from the analysis to an entity associated with the patient. Other variations and examples of the detection subsystem 150 can, however, be configured in any other suitable manner relative to the piston module 140.

Furthermore, the detection subsystem 150 can include any other suitable sensor modules configured to detect parameters of the scanning medium and/or environmental conditions within the inner chamber 110. Additionally or alternatively, the detection subsystem 150, the inner chamber 110, and/or any other suitable elements of the system 100 in communication with the inner chamber 110 can facilitate retention of the volume of tissue in position during scanning.

1.4 System—Actuator and Patient Interface

The actuator 160 comprises a stationary portion 161 mounted to the piston module 140, and a moving portion 162 coupled to the inner chamber 110 and configured to produce motion of the inner chamber along the motion path. The actuator 160 functions to enable positioning of the inner chamber 110, with the scanning medium and the transducer 120, relative to the volume of tissue being scanned in a controllable manner. The moving portion 162 of the actuator 160 is preferably a linear actuator that produces vertical motion of the inner chamber 110 and coupled transducer 120 along a vertical axis, such that the inner chamber 110 can move in a superior-to-inferior direction and an inferior-to-superior direction (e.g., in relation to the ground) along the vertical axis. However, the actuator 160 can be configured to produce motion along any other suitable motion path (e.g., a non-linear motion path, a motion path in multiple coordinate directions). Furthermore, the moving portion 162 can be coupled to plates that couple the moving portion 162 to electronic components of the system (e.g., electromechanical coupler 127, wires, etc.). In a first variation, the actuator 160 comprises a motor and lead screw mechanism, as the moving portion 162 coupled to the inner chamber 110, that provides motion of the inner chamber 110 and coupled transducer 120 along a vertical axis. In another variation, the moving portion 162 of the actuator 160 is configured to produce motion hydraulically. In yet another variation, the actuator 160 can comprise a scissor lift, as the moving portion 162, that produces linear motion. However, other variations of the actuator 160 can be configured to produce motion by any other suitable mechanism.

Travel along the motion path can be controlled using any one or more of limit switches, position encoders, and any other suitable element that tracks motion. For instance, the actuator 160 can be configured to cooperate with one or more limit switches that govern endpoints of the motion path, wherein the endpoints can be adjustable. Additionally or alternatively, the actuator 160 can be configured to cooperate with a position encoder (e.g., linear encoder, rotary encoder, Hall-effect sensor, etc.) configured to enable identification of a position of travel along the motion path. The actuator 160 can, however, be configured to cooperate with any other suitable element in order to produce motion along the motion path in a controllable manner. Furthermore, in some variations, a base 166 of the actuator 160 can be coupled to an adjustable mount that allows the actuator 160 to be positioned in a plane (e.g., an X-Y plane) and/or allows adjustment of pitch/yaw of the actuator 160.

As shown in FIG. 1B, the stationary portion 161 of the actuator 160 is preferably mounted to the piston module 140, such that the piston module 140 is substantially fixed in space. As such, the stationary portion 161 of actuator 160 preferably couples the piston module 140 to a support structure of the system 100, and in variations of the system 100 including a manifold 149, the stationary portion 161 can couple the piston module 140 to the manifold 149. However, the stationary portion 161 can additionally or alternatively couple the piston module 140 to any other suitable portion of the system 100 that is substantially non-moving. Furthermore, the moving portion 162 of the actuator 160 is preferably mounted to the inner chamber (e.g., using a coupling plate), such that the inner chamber 110 and coupled transducer 120 can move along the motion path enabled by the actuator 160. As such, the piston module 140 preferably does not move as the inner chamber 110 moves along the motion path, while hermetic seals are maintained using elements as described above. However, variations of the actuator 160 can alternatively produce motion of any or both of the inner chamber 110 and the piston module 140.

In some variations, the actuator 160 can be coupled to the inner chamber 110 and/or other moving elements of the system 100 with one or more isolation mounts 165 that allow motion in at least one direction or plane, while constraining other forms of motion. For instance, in one variation, as shown in FIG. 4A, the inner chamber 110 can be coupled to peripherally located isolation mounts 165 which are coupled to the moving portion of the actuator 160 (e.g., using a plate coupler), wherein the isolation mounts 165 allow the inner chamber 110 to "float" laterally with some freedom while constraining motion of the inner chamber 110 along a vertical axis (in the orientation shown in FIG. 4A). In this variation, such a configuration prevents the piston module 140 from being over constrained and/or binding during motion of the inner chamber 110. Other variations of the system 100 can include isolation mounts 165 coupled to any other suitable element of the system (e.g., the outer chamber 130, as shown in FIG. 3B) in order to allow freedom of motion in one or more directions, while constraining motion of others.

As shown in FIGS. 1A and 1B, the system 100 can further comprise a patient support surface 170 coupled to the outer chamber 130 and having an opening 172 (as shown in FIG. 3B) that facilitates reception of the volume of tissue into the inner chamber 110. The patient support surface 170 is preferably configured to interface with a patient interface system that receives a prone patient in a configuration that allows protruding tissue of the patient to enter the opening of the patient support surface 170 for scanning. As such, in some embodiments, the system 100 can interface with the patient interface system described in U.S. application Ser. No. 14/208,181, entitled "Patient Interface System" and filed on 13 Mar. 2014, which is incorporated herein in its entirety by this reference; however, the system 100 can additionally or alternatively be configured to interface with any other suitable system to facilitate scanning of a volume of tissue protruding from a patient's body. In some variations, wherein the patient support surface 170 is configured to interface with a variation of the patient interface system described in U.S. application Ser. No. 14/208,181, the patient support surface 170 can comprise a frustoconical surface with a centrally located opening 172 that aligns with the patient interface system and facilitates reception of the volume of tissue. In a specific example, the patient support surface 170 can be welded to the outer chamber 130 with face-sealing rings (e.g., O-rings) to provide a hermetic seal against scanning medium that leaves the inner chamber and enters a region defined by the patient support surface; however, the patient support surface 170 can alternatively be coupled to any other element(s) of the system 100 in any other suitable manner.

Embodiments of the system 100 can include any other suitable elements that facilitate provision of scanning medium and a transducer 120 to enable scanning of a volume of tissue of a patient in a controlled manner. For instance, system 100 can include one or more level sensors that facilitate identification of one or more amounts of scanning medium within the system 100. In one example, as shown in FIG. 3A, the system 100 can include a first level sensor 176 in communication with an inlet into the inner chamber 110, and a second level sensor 177 coupled to a patient support surface 170, such that the first level sensor 176 enables identification of an empty state and the second level sensor 177 enables identification of a full state in relation to scanning medium within the inner chamber. The level sensors can, however, be coupled to or otherwise able to detect a level of the scanning medium in any other suitable manner.

In some variations, an example of which is shown in FIG. 3A, the system 100 can additionally or alternatively include a chamber 178, coupled about one or more of the inner chamber 110, the outer chamber 130, and the patient support surface 170, that functions as a reservoir for splash overflow protection, in the event that scanning medium enters a region of the system 100 in an undesirable manner. As such, in the example, the chamber 178 can capture any portion of the scanning medium that spills over the patient support surface 170, thereby preventing scanning medium from adversely affecting other components of the system 100. The system 100 can, however, include any other suitable element(s).

Embodiments of the system 100 and variations thereof can be embodied and/or implemented at least in part by a machine configured to receive a computer-readable medium storing computer-readable instructions. The instructions are preferably executed by computer-executable components preferably integrated with the system 100 and one or more portions of a processor and/or a controller. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

The FIGURES illustrate the architecture, functionality and operation of possible implementations of systems, methods and computer program products according to preferred embodiments, example configurations, and variations thereof. In this regard, each block in a flowchart or block diagram may represent a module, segment, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A system for providing a scanning medium for scanning a volume of tissue of a patient, the system comprising:
    an inner chamber configured to contain the scanning medium;
    a ring transducer within the inner chamber and configured to move along a motion path in scanning the volume of tissue, wherein the ring transducer comprises an array of ultrasound emitters and an array of ultrasound receivers configured to surround the volume of tissue;
    a piston module having a base surface within the inner chamber, the piston module including a medium inlet and a medium outlet for adjusting an amount of the scanning medium within the inner chamber, and wherein an interface between the piston module and the inner chamber is hermetically sealed as the inner chamber moves along the motion path;
    a detection subsystem coupled to the base surface of the piston module and comprising an optical sensor module fluidly isolated from the scanning medium within the inner chamber; and
    an actuator module comprising 1) a stationary portion mounted to the piston module and 2) a moving portion coupled to the inner chamber and configured to produce motion of the inner chamber along the motion path.

2. The system of claim 1, wherein the ring transducer is mounted to a superior portion of the inner chamber, and wherein the inner chamber and the ring transducer are configured to move along a posterior-to-anterior axis of the volume of tissue in a first operation mode.

3. The system of claim 2, further comprising a transducer mount that comprises a plurality of drainage ports configured to allow the scanning medium to flow during movement of the transducer.

4. The system of claim 1, wherein the detection subsystem further comprises a temperature sensor proximal at least one of the medium inlet and the medium outlet, and wherein the optical sensor module is configured to transmit image data of the volume of tissue, during scanning, to a computing system.

5. The system of claim 4, further comprising an array of light emitters surrounding the optical sensor module and configured to indicate proper function of the system, wherein the optical sensor module and the array of light emitters are isolated from the scanning medium within the inner chamber by way of a transparent covering mounted to the piston module.

6. The system of claim 1, wherein the medium inlet comprises a fitting that directs the scanning medium laterally into the inner chamber, and wherein the medium outlet is in communication with an anti-vortex fitting that prevents generation of a fluid eddy as the scanning medium is drained from the inner chamber.

7. The system of claim 1, wherein the ring transducer moves along the motion path with the inner chamber.

8. The system of claim 1, wherein the inner chamber comprises an inner chamber aperture sized and shaped to receive the volume of tissue.

9. The system of claim 8, wherein the inner chamber is configured to receive the volume of tissue when the patient is prone.

10. The system of claim 1, wherein the volume of tissue is a patient breast.

11. The system of claim 1, wherein the inner chamber is configured to move within an outer chamber.

12. The system of claim 11, wherein the outer chamber is concentrically aligned with the inner chamber.

13. The system of the claim 11, wherein the system further comprises a seal in contact with the inner chamber and the outer chamber and wherein the seal prevents leakage of the scanning medium between the outer chamber and the inner chamber.

14. The system of claim 13, wherein the seal is coupled to the inner chamber and is configured to move with the inner chamber.

15. The system of claim 13, wherein the seal is coupled to the outer chamber and remains stationary as the inner chamber moves along the motion path.

16. The system of claim 11, further comprising a frustoconical patient interface coupled to the outer chamber and including an interface aperture sized and shaped to receive the volume of tissue.

17. The system of claim 16, wherein the frustoconical patient interface comprises a level sensor configured to indicate a full state of the scanning medium within the inner chamber.

18. The system of claim 16, wherein the frustoconical patient interface is coupled to an overflow chamber, wherein the overflow chamber is configured to receive the scanning medium in the event of splash or overflow.

19. The system of claim 16, wherein the frustoconical patient interface comprises a patient support surface that aligns with the frustoconical patient interface and facilitates reception of the volume of tissue.

* * * * *

UNITED STATES PATENT AND TRADEMARK OFFICE
CERTIFICATE OF CORRECTION

| | |
|---|---|
| PATENT NO. | : 10,251,622 B2 |
| APPLICATION NO. | : 16/113863 |
| DATED | : April 9, 2019 |
| INVENTOR(S) | : Mike Tesic et al. |

It is certified that error appears in the above-identified patent and that said Letters Patent is hereby corrected as shown below:

In the Specification

In Column 1, Line 12, insert following header and paragraph:
--STATEMENT AS TO FEDERALLY SPONSORED RESEARCH
This invention was made with Government support under Grant R44CA165320 awarded by the National Institutes of Health (NIH) through the National Cancer Institute. The Government has certain rights in the invention.--

Signed and Sealed this
Thirtieth Day of July, 2024

Katherine Kelly Vidal
*Director of the United States Patent and Trademark Office*